(12) United States Patent
Propp

(10) Patent No.: US 8,212,101 B2
(45) Date of Patent: Jul. 3, 2012

(54) WINDOW DRESSING HAVING INTEGRAL ANCHOR

(75) Inventor: Donald J. Propp, Dewitt, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 178 days.

(21) Appl. No.: 12/695,440

(22) Filed: Jan. 28, 2010

(65) Prior Publication Data

US 2010/0198161 A1 Aug. 5, 2010

Related U.S. Application Data

(60) Provisional application No. 61/206,683, filed on Feb. 3, 2009.

(51) Int. Cl.
*A61F 5/00* (2006.01)
(52) U.S. Cl. ............... 602/58; 602/41; 602/42; 602/52; 604/180
(58) Field of Classification Search .......... 604/179, 604/180; 602/41–59; D24/189
See application file for complete search history.

(56) References Cited

U.S. PATENT DOCUMENTS

| | | | |
|---|---|---|---|
| 5,885,254 A * | 3/1999 | Matyas | 604/180 |
| 6,124,520 A * | 9/2000 | Roberts | 602/54 |
| 6,124,521 A * | 9/2000 | Roberts | 602/54 |
| 6,841,715 B2 * | 1/2005 | Roberts | 602/54 |
| 7,025,749 B2 * | 4/2006 | Propp | 604/180 |
| 7,294,752 B1 * | 11/2007 | Propp | 602/58 |
| 7,626,070 B2 * | 12/2009 | Propp | 602/41 |
| 7,674,948 B2 * | 3/2010 | Propp et al. | 602/58 |
| 7,723,561 B2 * | 5/2010 | Propp | 602/58 |
| 7,812,212 B2 * | 10/2010 | Propp et al. | 602/58 |
| 2004/0220505 A1 * | 11/2004 | Worthley | 602/54 |
| 2005/0261623 A1 * | 11/2005 | Propp | 604/19 |
| 2007/0060892 A1 * | 3/2007 | Propp | 604/180 |
| 2008/0058692 A1 * | 3/2008 | Propp et al. | 602/54 |
| 2008/0132821 A1 * | 6/2008 | Propp et al. | 602/54 |
| 2009/0192470 A1 * | 7/2009 | Propp | 604/180 |
| 2010/0004680 A1 * | 1/2010 | Propp | 606/213 |
| 2010/0121282 A1 * | 5/2010 | Propp | 604/180 |

* cited by examiner

*Primary Examiner* — Kim M Lewis
(74) *Attorney, Agent, or Firm* — Bill C. Panagos; Linda D. Kennedy; Rader, Fishman & Grauer PLLC

(57) ABSTRACT

A window dressing includes a fabric layer having juxtaposed insertion site viewing and anchor member portions. The fabric layer has an adhesive side and an opposite non-adhesive top side. The insertion site viewing portion is defined by an opening in the fabric layer. A transparent film layer having an adhesive skin-adhering, bottom, side and an opposite non-adhesive side is adhered to the fabric layer adhesive side and closes the opening in the fabric layer. The anchor member portion includes a reinforcing structure disposed on the fabric layer and having an adhesive side and an opposite non-adhesive side. The reinforcing structure adhesive side is adhered to the fabric layer non-adhesive top side.

17 Claims, 11 Drawing Sheets

WINDOW DRESSING HAVING INTEGRAL ANCHOR

CROSS REFERENCE TO RELATED APPLICATION

This application claims the priority of U.S. Provisional Application No. 61/206,683 filed Feb. 3, 2009.

TECHNICAL FIELD

This invention relates to medical dressings, and more particularly to self-adherent window dressings for the viewing, protection, and securement of PICC, CVC, IJ, subclavian, femoral, and implant port catheters about an insertion site.

BACKGROUND OF THE INVENTION

It is known in the art relating to medical dressings for the protection and securement of catheters to apply a dressing to a patient's skin to cover a catheter insertion site at which the catheter punctures a patient's skin. It is also common for medical clinicians (i.e., doctors, nurses, and other medical personnel) to alternatively or additionally apply strips of medical grade tape to attempt to secure the catheter or associated medical tubing. Another conventional clinical practice is to suture a catheter hub to a patient's skin to roughly secure the catheter to the patient. Further still, a variety of catheter and medical tubing securement devices are available for use in the medical field. These securement devices, however, are often bulky and cumbersome, hard to dress with a dressing, and may have costly and complex mechanical features.

Although a wide variety of medical dressings and catheter and tubing securement devices are commercially available, individual clinicians tend to prefer to use one or a few dressings and securement devices for multiple and often unintended applications. Therefore, the dressing or securement device used is often too big or too small for the insertion site and surrounding bodily contours, or may simply have a design structure that is functionally incompatible with the application. This self-customization by clinicians therefore leads to poor catheter securement and protection.

Furthermore, it is also known in the medical field that poorly dressed and poorly secured catheters and associated tubing are likely to undesirably lead to irritation of the insertion site, necessitating movement of the catheter to a new insertion site. Even worse, poorly secured catheters are susceptible to accidental dislodgement from the insertion site. For example, medical tubing connected to indwelling catheters, infusion needles and the like is often subjected to inadvertent but significant pulling forces either caused directly by patient movement or by snagging of the tubing on other objects. These pulling forces peel the medical tape or dressing securing the catheter and/or tubing off the patient's skin. This exposes the catheter, infusion needle, etc. to movement inward or outward, increasing the likelihood that the catheter, infusion needle, etc. will fail and have to be replaced and inserted into a new insertion site. Also, this may weaken the adhesion between the dressing and the patient's skin, potentially exposing the insertion site to harmful bacteria.

SUMMARY OF THE INVENTION

The present invention provides a multi-use, "universal" medical dressing having an integral anchor for use in protecting an array of catheter insertion sites, such as PICC sites, CVC sites, IJ sites, subclavian sites, femoral sites, and implant port infusion needle sites. The present medical dressing is capable of securing a variety of catheters, infusion needles, and associated hubs, connectors, ports, and tubing.

More particularly, a window dressing in accordance with the invention includes a fabric layer having juxtaposed insertion site viewing and anchor member portions. The fabric layer has an adhesive side and an opposite non-adhesive side. The insertion site viewing portion is defined by an opening in the fabric layer. A transparent film layer having an adhesive skin-adhering side and an opposite non-adhesive side is adhered to the fabric layer adhesive side and closes the opening in the fabric layer. The anchor member portion includes a reinforcing structure disposed on the fabric layer and having an adhesive side and an opposite non-adhesive side. The reinforcing structure adhesive side is adhered to the fabric layer non-adhesive side such that the reinforcing structure is on top of the fabric layer.

The reinforcing structure may include a central body and a plurality of spaced ribs extending outwardly from the central body. The reinforcing structure may include an opening in the central body. The reinforcing structure may be generally symmetric about one of its axes. The anchor member portion of the fabric layer may include an opening therein, and the opening may be generally surrounded by the reinforcing structure.

A pad member may generally circumscribe the viewing portion opening and may be adhered to the film layer adhesive side. A U-shaped slot may extend inwardly from an edge of the fabric layer. A perforation line in the anchor member portion may extend from one edge of the dressing to another edge of the dressing, wherein the dressing is separable into two pieces. A pair of side perforation lines may each extend inwardly from an edge of the fabric layer proximate the opening, and may be generally perpendicular to the fabric layer edge. A landmark notch may be disposed along the fabric layer edge at an end of each side perforation line. The dressing may be symmetrical about a longitudinal axis.

The reinforcing structure may be colored. An adhesive on the reinforcing structure adhesive side may include a colorant. A colorant may be disposed on the reinforcing structure non-adhesive side. The reinforcing structure may include a colorant therein.

The transparent film layer may extend to an outer edge of the fabric layer. An outer edge of the fabric layer may extend beyond the transparent film layer.

In another embodiment, a window dressing in accordance with the invention includes a fabric layer having juxtaposed insertion site viewing and anchor member portions. The fabric layer has an adhesive side and an opposite non-adhesive side. The insertion site viewing portion may be defined by an opening in the fabric layer. A transparent film layer having an adhesive skin-adhering side and an opposite non-adhesive side is adhered to the fabric layer adhesive side and closes the opening in the fabric layer. The anchor member portion includes a reinforcing structure disposed on the transparent film layer. The reinforcing structure is adhered to the transparent film layer adhesive side.

In yet another embodiment, a window dressing in accordance with the invention includes a transparent film layer having juxtaposed insertion site viewing and anchor member portions. The transparent film layer also has an adhesive skin-adhering side and an opposite non-adhesive side. The anchor member portion includes a reinforcing structure disposed on the transparent film layer and having an adhesive side and an opposite non-adhesive side. The reinforcing structure adhesive side is adhered to the transparent film layer non-adhesive side.

In yet another embodiment, a window dressing in accordance with the invention includes a transparent film layer having juxtaposed insertion site viewing and anchor member portions. The transparent film layer also has an adhesive skin-adhering side and an opposite non-adhesive side. The anchor member portion includes a reinforcing structure disposed on the transparent film layer. The reinforcing structure is adhered to the transparent film layer adhesive side.

These and other features and advantages of the invention will be more fully understood from the following detailed description of the invention taken together with the accompanying drawings.

DETAILED DESCRIPTION OF THE INVENTION

Figure 1:
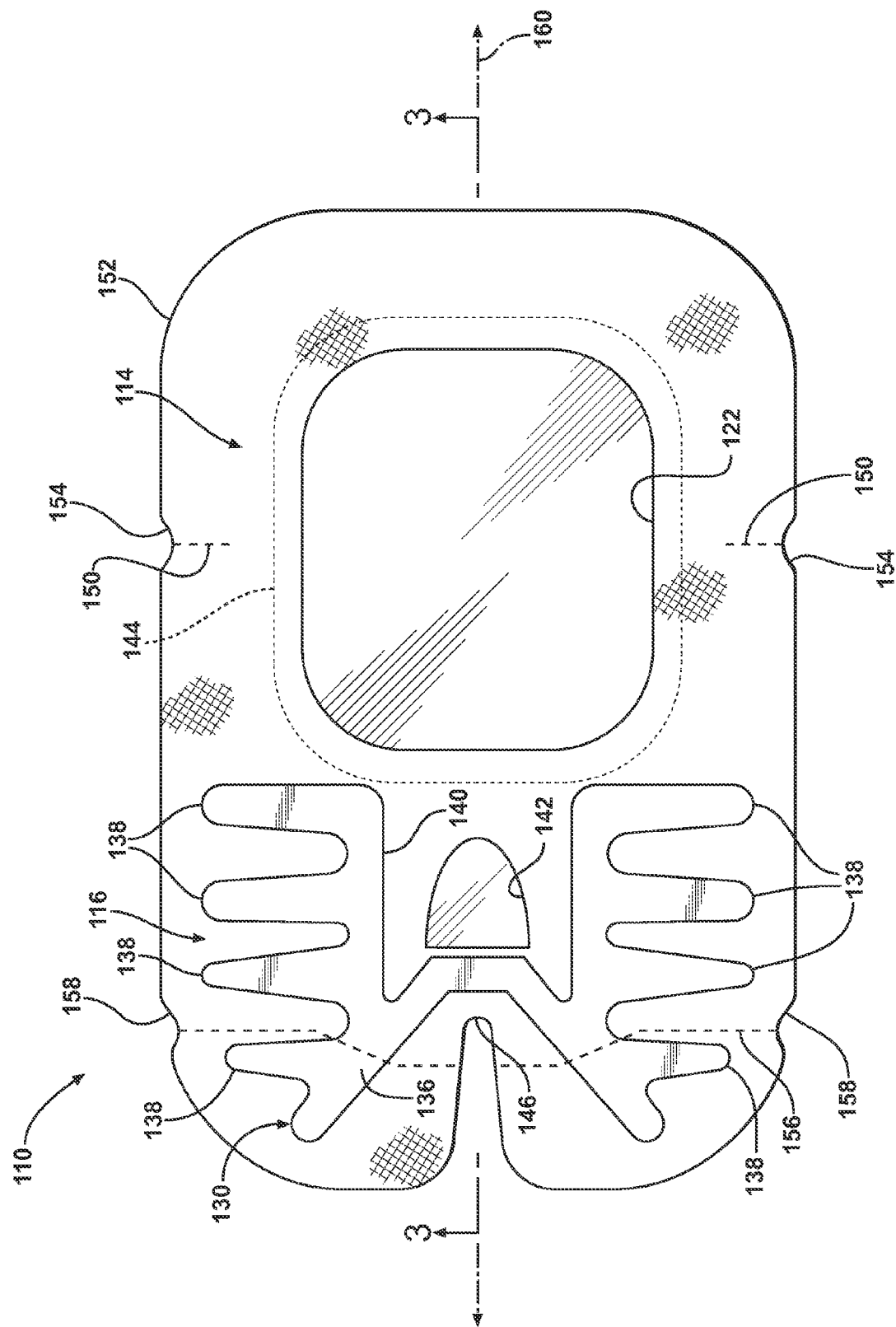
FIG. 1 is a plan view of a window dressing with integral anchor in accordance with the present invention.
Figure 2:
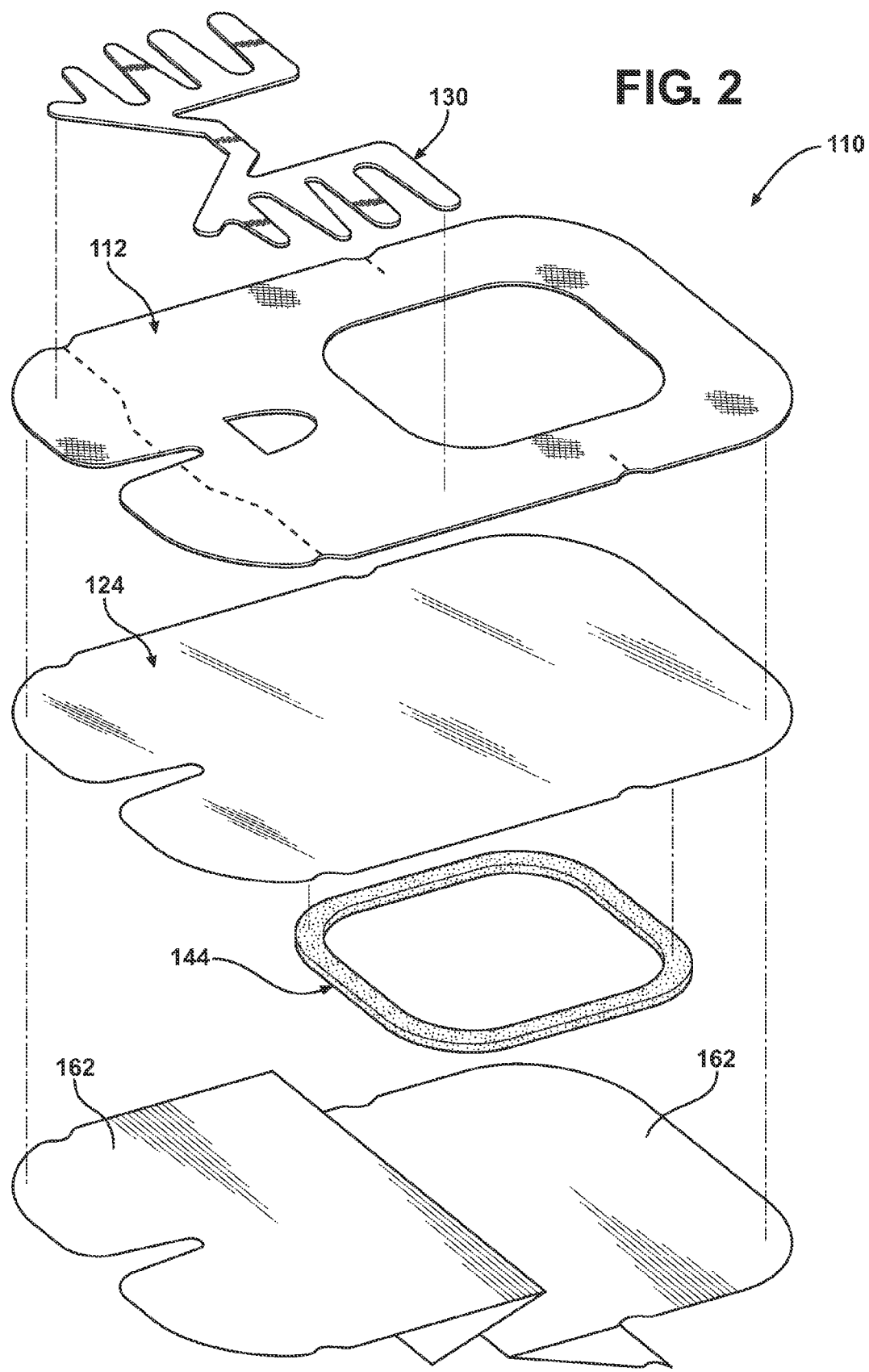
FIG. 2 is an exploded view of the window dressing of FIG. 1.
Figure 3:
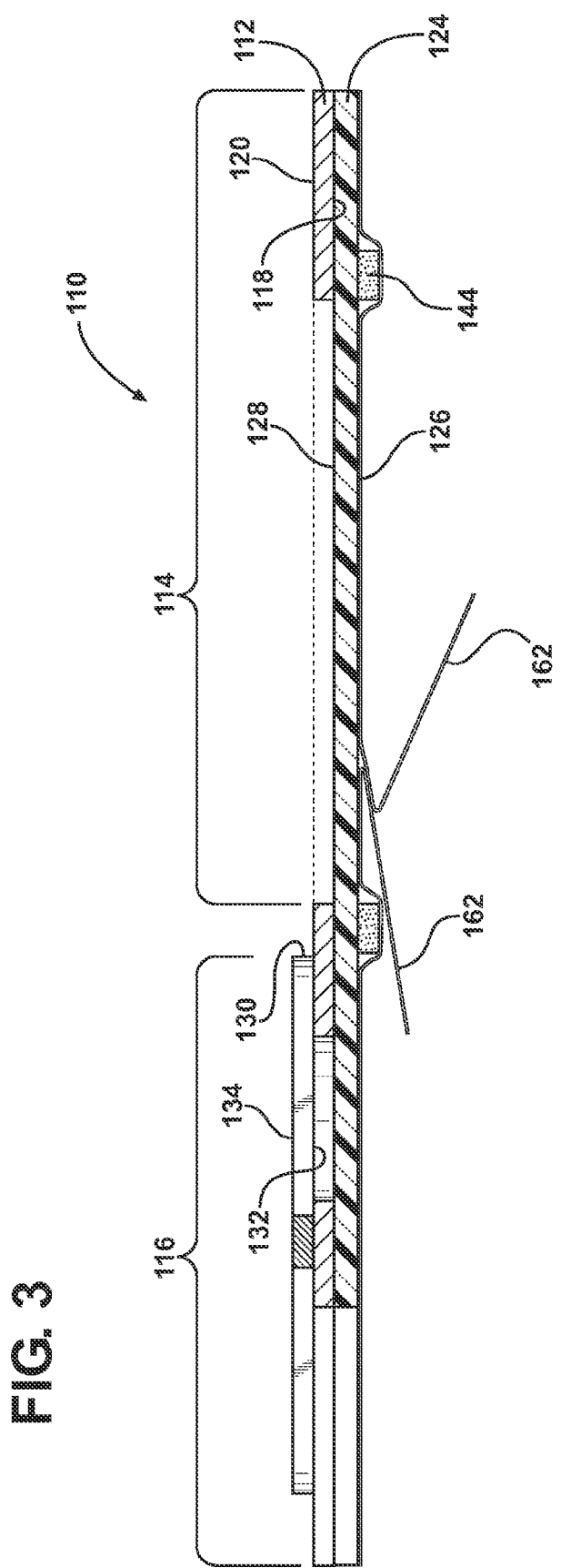
FIG. 3 is a cross-sectional view of the window dressing taken along the line 3-3 in FIG. 1.
Figure 4:
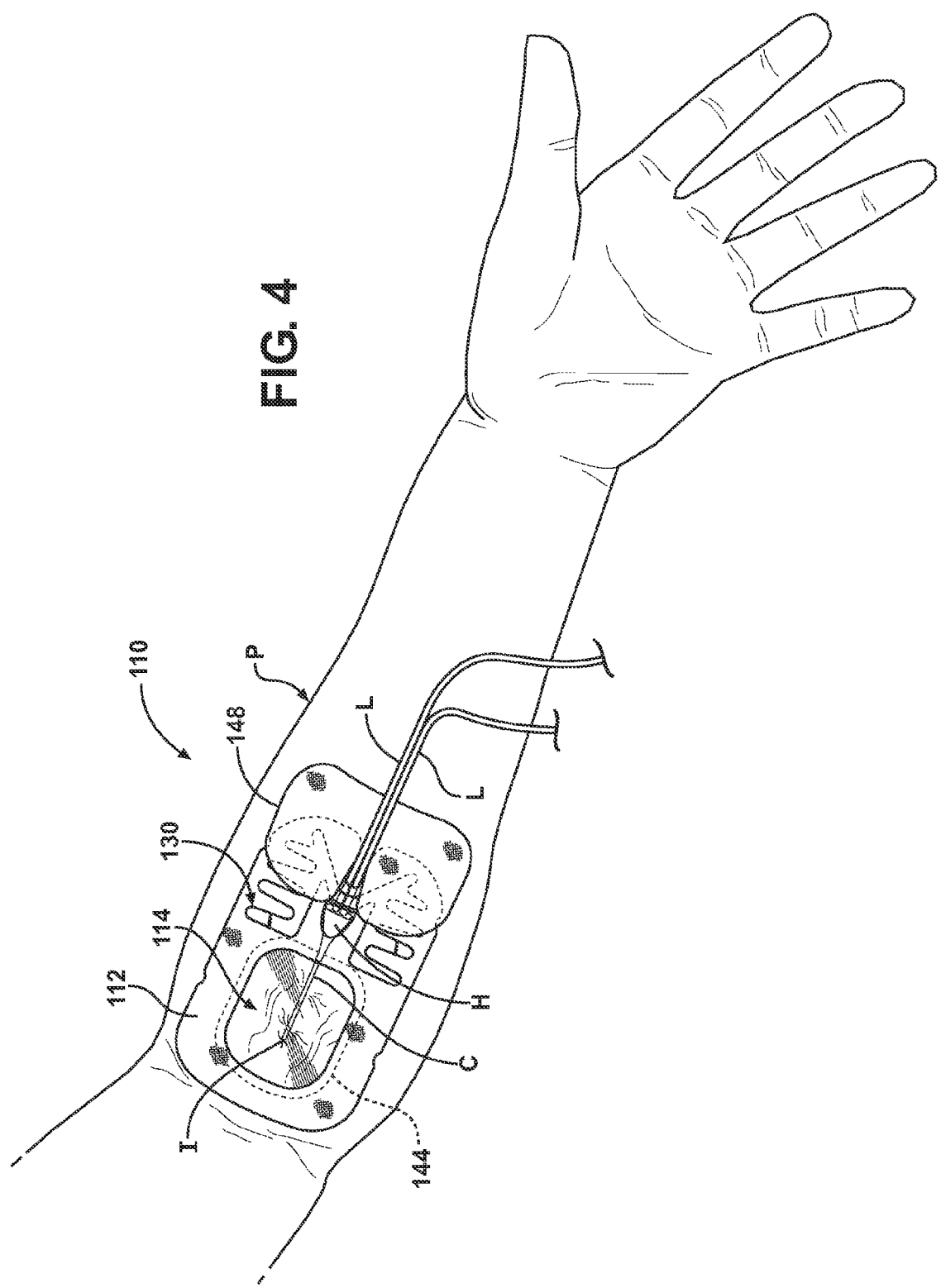
FIG. 4 is an environmental view the window dressing of FIG. 1 securing and protecting a double lumen catheter, and an auxiliary removable securement device anchoring under the catheter's two pigtail tubings.

Referring now to the drawings in detail, a window dressing 110 with an integral anchor member that may be used to view, protect, and secure a catheter inserted into a catheter insertion site such as a PICC ("peripherally inserted central venous catheter") insertion site, a jugular insertion site, a subclavian insertion site, a femoral insertion site, or an implanted port insertion site is illustrated. The medical window dressing 110 is capable of securing a variety of sizes, shapes, and types of catheters (single lumen, double lumen, triple, and quad lumen), infusion needles, and associated hubs, ports, and tubing. The window dressing 110 provides protection against microbial ingress and site or patient systemic infection, and secures the catheter and associated hubs, ports, and tubing so that forces acting on the tubing and catheter do not peel the dressing from a patient's skin or cause the catheter to become dislodged.

With reference to FIGS. 1 through 4, the window dressing 110 includes a fabric layer 112 having an insertion site viewing portion 114 and an anchor member portion 116 that are juxtaposed. The fabric layer 112 may be a woven or non-woven material. The fabric layer 112 has an adhesive side 118 and an opposite non-adhesive top side 120. The "top" side refers to an upper (or outer) side when the dressing is disposed on a patient's skin (for example, see FIG. 4). The adhesive side 118 may be coated with any suitable medical grade adhesive. The insertion site viewing portion 114 is defined by an opening 122 in the fabric layer. A transparent film layer 124 having an adhesive skin-adhering side 126 and an opposite non-adhesive side 128 is adhered by its non-adhesive side to the fabric layer adhesive side 118. The transparent film layer 124 closes the opening 122 in the fabric layer 112. The transparent film layer 124 may be a polyurethane film coated on one side with any suitable medical grade adhesive. The anchor member portion 116 includes an anchor member that may be a reinforcing structure 130 disposed on the fabric layer 112. The reinforcing structure 130 has an adhesive side 132 and an opposite non-adhesive side 134. The reinforcing structure adhesive side 132 is adhered to the fabric layer non-adhesive side 120 such that the reinforcing structure is on top of the fabric layer 112. The reinforcing structure 130 may be made of a polypropylene net material, a net-like material, or another similar material having rigidizing and force spreading properties as discussed below.

Since the reinforcing structure 130 is on top of the fabric layer 112, it is easier for a clinician or other user to see the reinforcing structure for proper application of the dressing around a catheter, hub, and tubing on a patient's skin. The reinforcing structure needs to be properly positioned relative to the catheter hub and tubing in order to provide maximum securement of the dressing. Also, it is easier to manufacture the dressing with the reinforcing structure on top of the fabric layer rather than sandwiched between the fabric layer and the transparent film layer.

The reinforcing structure 130 may be any shape that has multiple axes such as an X-shape, another similar hub-and-spoke shape, or a backbone and rib shape. In one specific embodiment, the reinforcing structure 130 may include a central body 136 and a plurality of spaced ribs 138 extending outwardly from the central body. The reinforcing structure 130 may also include an opening 140 in the central body 136. The opening 140 allows for the reinforcing structure to generally surround a catheter hub without lying directly on top of the hub. The reinforcing structure 130 may be generally symmetric about one of its axes. The central body 136 of the reinforcing structure 130 may be generally shield-shaped.

The reinforcing structure 130 strengthens the dressing 110 by making it less floppy for easier application to a patient's skin. More importantly, when the dressing is applied to a patient's skin, the reinforcing structure spreads the external forces that are exerted on the dressing by the tubing over a large surface area, greatly increasing the dressing's resistance to premature separation from the patient's skin. Likewise, the reinforcing structure increases the amount of force necessary to separate the dressing from a patient's skin. External forces are not as localized which is the typical reason small forces are able to commence peeling of a dressing by stretching the fabric and film in a local area which then propagates onward. Commonly, external forces are exerted on the dressing by pulling, snagging, or tugging on the ports, pigtails, fittings, and/or medical tubing that are connected to the catheter hub. For example, movement of the medical tubing may be caused by the patient moving, by snagging of the tubing on other neighboring objects, by a clinician moving the tubing or the patient, or any combination of the above. The reinforcing structure also prevents premature separation of the dressing from a patient's skin by preventing the dressing from stretching when the dressing is tugged on as described above, for example, when the tubing connected to the catheter hub is pulled on. Stretching of a dressing locally can ultimately lead to a dressing separating fully from a patient's skin. In sum, the reinforcing structure increases the withstand of the dressing and greatly increases the amount of multi-directional pulling force that is necessary to cause the dressing to separate from a patient's skin.

The window dressing 110 may also include an opening 142 in the anchor member portion 116 of the fabric layer 112 that is generally surrounded by the reinforcing structure 130. Specifically, the opening 142 may be generally surrounded by the central body 136 of the reinforcing structure 130. The opening 142 in the anchor member portion 116 may be smaller in area than the opening 122 in the insertion site viewing portion 114. The transparent film layer 124 closes the opening 142 to form a window for viewing therethrough. The anchor member portion opening 142 allows for the viewing of the catheter hub so that a clinician may read the manufacturer part number or gage printed on the hub. Further, the opening 142 allows for viewing of the skin so that a clinician can ascertain whether any irritation, redness, or maceration is occurring under or at the perimeter of the catheter hub. Moreover, if the catheter hub is also secured to the patient's skin by sutures, the opening allows for viewing of the sutures to ascertain whether the sutures remain intact. Even more, the transparent film layer 124, which is very elastic, in closing the opening rises up and stretches over a catheter hub when the dressing 110 is applied to a patient. This causes a pocket to be formed for the hub and traps the central body 136 of the reinforcing structure 130 behind the hub, further securing the hub and preventing movement of the hub when the hub is subjected to pulling forces exerted by the tubing connected to the hub. At extreme, but not atypical, tug forces on the pigtail tubing, the hub may try to slide back, but the back end of reinforcement structure hits the back of the hub, effectively "snagging it," then requiring all of the net structure to come free before any further hub motion can occur. A very high force is needed to do this. This very high security is created 50 to 100% more than current devices.

A pad member 144 may be adhered to the film layer adhesive side 126 and may generally circumscribe the viewing portion opening 122. The pad member 144 may be relatively thin and may have a low absorbent capacity, such as a capacity of approximately 2-3 cc. The pad member 144, however, is capable of preventing the egress of certain amounts of exudate and other liquids from beyond the viewing portion. It is not necessary for the pad 144 to have a large absorbent capacity for most typical catheters and insertion sites. It is likely that in practice the dressing would be replaced before or at the time that a small amount of exudate has been absorbed by the pad.

A U-shaped slot 146 may extend inwardly from an edge of the fabric layer 112. The U-shaped slot 146 may be disposed in the anchor member portion 116 proximate the reinforcing structure 130. The U-shaped slot 146 provides a location for tubing to exit from underneath the dressing 110 and helps secure the tubing in place. A tape strip closure member 148 may be secured across the U-shaped slot 146, underneath the tubing and snug against the tubing, for increased securement of the dressing at the tubing exit.

The window dressing 110 may further include a pair of side perforation lines 150. Each side perforation line 150 extends inwardly from an edge 152 of the fabric layer 112 proximate the opening 122, and may be generally perpendicular to the fabric layer edge. A landmark notch 154 may be disposed along the fabric layer edge 152 at an end of each side perforation line. The side perforation lines 150 may be separated and opened prior to application of the dressing in order to more effectively anchor tubing extending from sideported catheter hubs such as a sideported CVC. Each of the pair of side perforation lines 150 may be disposed symmetrically on opposite sides of the dressing, allowing the dressing to accommodate either left-handed or right-handed sideports. In a specific embodiment, the side perforation lines 150 may be disposed on opposite sides of the opening 122 of the window viewing portion 114. The landmark notches 154 aid a clinician or other user in locating the ends of the side perforation lines 150 when it is necessary or desirable to tear one of the side perforation lines.

A removal perforation line 156 in the anchor member portion 116 may extend from one edge (lateral side) of the dressing to another edge (lateral side) of the dressing 110, wherein the dressing is separable into two pieces. A landmark notch 158 may be disposed along the fabric layer edge 152 at each end of the perforation line 156. The landmark notches 158 help a clinician or other user of the dressing locate the ends of the perforation line 156 when it is necessary to tear the perforation line. The perforation line 156 may be torn when it is desired to shorten the length of the dressing 110 for certain patient applications that require a shorter dressing length.

The reinforcing structure 130 may be colored. An adhesive on the reinforcing structure adhesive side 132 may include a colorant, or a colorant may be disposed on the reinforcing structure non-adhesive side 134. Alternatively, the reinforcing structure 130 may include a colorant therein. For example, the colorant may be directly added to the raw material from which the reinforcing structure 130 is made. The colorant improves the visibility of the reinforcing structure 130 and greatly aides in proper placement of the dressing 110 on a patient's skin such that the reinforcing structure is properly disposed relative to a catheter hub, tubing, etc.

Figure 5:
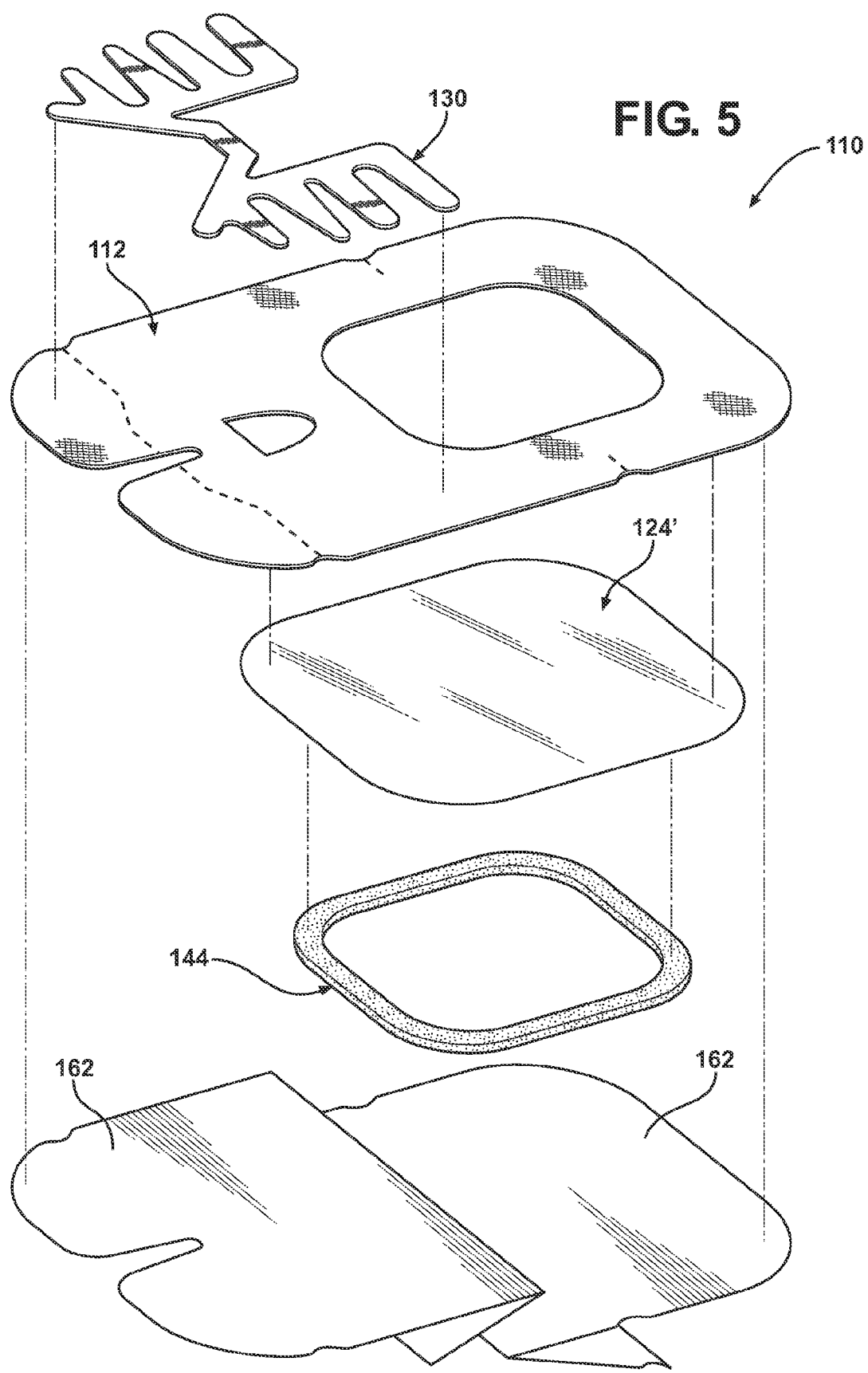
FIG. 5 is an exploded view of an alternative embodiment of the dressing of FIG. 1 in which a film layer of the dressing does not extend to an outer edge of a fabric layer of the dressing.

The transparent film layer 124 may extend to the outer edge 152 of the fabric layer 112. Alternatively, as shown in FIG. 5, the transparent film layer 124' may not extend all the way to the outer edge of the fabric layer such that the outer edge of the fabric layer may extend beyond the transparent film layer 124'.

The dressing 110 may be symmetrical about a longitudinal axis 160 that extends through the insertion site viewing portion 114 and the anchor member portion 116, and splits the dressing into equivalent left-hand and right-hand sides. The symmetry of the dressing 110 allows the dressing to be used on either the left-hand or right-hand side of a patient's body.

A release liner 162 may cover the film layer adhesive side 126 of the insertion site viewing portion 114 and anchor member portion 116. The release liner 162 prevents the adhesive on the film layer 124 from inadvertently and prematurely sticking to an object prior to application. In a specific embodiment, the release liner 162 may be a two piece, V-fold butterfly type release liner. In this embodiment, each piece of the release liner covers a portion of the dressing. Each piece of the release liner also includes a tab portion folded on top of itself. The tab portions may be gripped by a clinician for easy removal of the release liner prior to application of the dressing.

As described above, other geometries of the dressing may deviate greatly from this specific embodiment and will accomplish similar tug withstand performance.

To apply the dressing 110 to an insertion site I on a patient P, the portion of the release liner 162 covering the insertion site viewing portion 114 of the dressing is peeled back to expose the adhesive on the transparent film layer 124. The insertion site viewing portion 114 is centered about the catheter insertion site I on the patient P so that the insertion site is generally in the center of the opening 122. This allows the insertion site I to be easily viewed through the opening 122. At the same time, the catheter hub H is blindly centered approximately underneath the opening 140 in the central body 136 of the reinforcing structure 130 so that the hub may be viewed through the opening 142 in the anchor member portion 116 of the dressing 110. The opening 140 must be blindly aligned with the catheter hub H because at this step the release liner 162 still covers the opening 142. The properly aligned insertion site viewing portion 114 is then adhered to the patient's skin.

Next, the portion of the release liner 162 covering the anchor member portion 116 is removed by grasping the tab of the release liner and pulling away from the insertion site viewing portion 114. The tubing L connected to the hub H is generally arranged to exit from underneath the dressing 110.

A tape strip closure member 148 may be placed snugly under tubing L that exits from the dressing at the U-shaped slot 146, and the tape strip also extends over the edge 152 of the dressing. The closure member 148 further prevents tugging or pulling forces on the tubing L from disturbing the dressing 110 and likewise the catheter C and catheter hub H located about the insertion site I.

To remove the dressing 110, a tape strip or similar may be used to secure the tubing L at a location spaced from the dressing. The dressing 110 can then be removed from the patient's skin by a single gentle pull motion from the "back" of the dressing adjacent the anchor member portion 116 towards the insertion site viewing portion 114.

Figure 6:
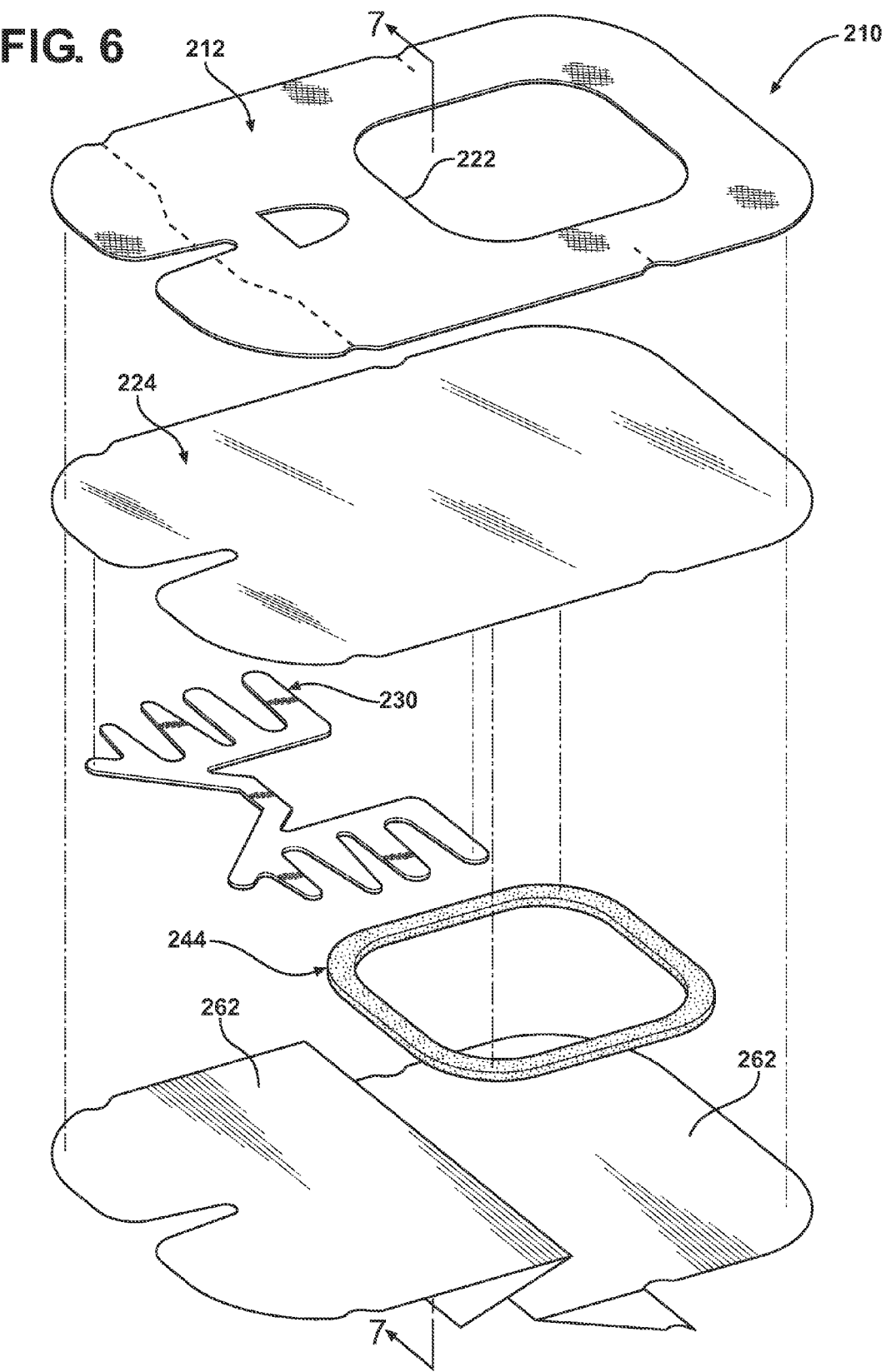
FIG. 6 is an exploded view of an alternative embodiment of a dressing with integral anchor in accordance with the present invention.
Figure 7:
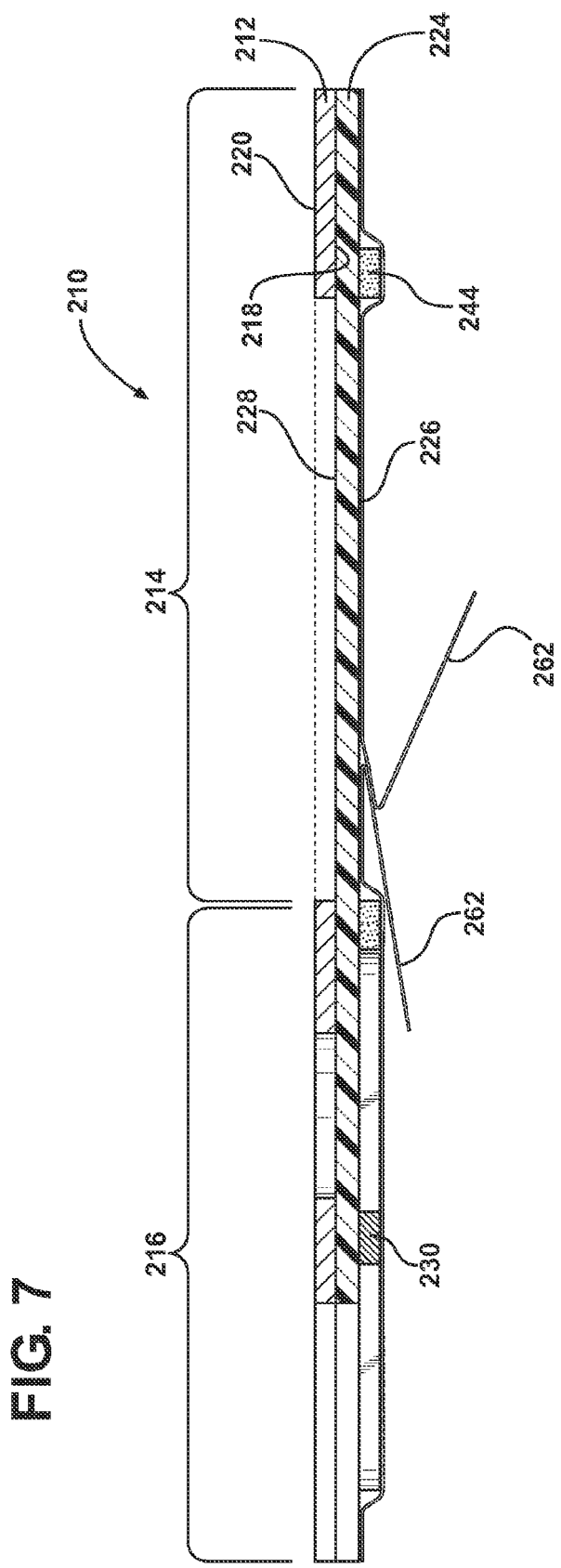
FIG. 7 is a cross-sectional view of the dressing of FIG. 6 taken along the line 7-7 in FIG. 6.

In another embodiment shown in FIGS. 6 and 7, a window dressing 210 in accordance with the invention includes a fabric layer 212 having juxtaposed insertion site viewing 214 and anchor member 216 portions. The fabric layer 212 has an adhesive side 218 and an opposite non-adhesive side 220. The insertion site viewing portion 214 may be defined by an opening 222 in the fabric layer 212. A transparent film layer 224 having an adhesive skin-adhering bottom side 226 and an opposite non-adhesive side 228 is adhered to the fabric layer adhesive side 218 and closes the opening 222 in the fabric layer 212. The bottom side of the transparent film layer 224 refers to a lower side of the transparent film layer when the dressing 210 is disposed on a patient's skin, i.e. the bottom side faces the patient's skin. The anchor member portion 216 includes an anchor member such as a reinforcing structure 230 disposed on the transparent film layer 224. The reinforcing structure 230 is adhered to the transparent film layer adhesive side 226, i.e., the bottom side of the transparent film layer 224. A pad member 244 may be adhered to the film layer adhesive side 226 and may generally circumscribe the viewing portion opening 222. A release liner 262 may cover the film layer adhesive side 226 of the insertion site viewing portion 214 and anchor member portion 216.

Figure 8:
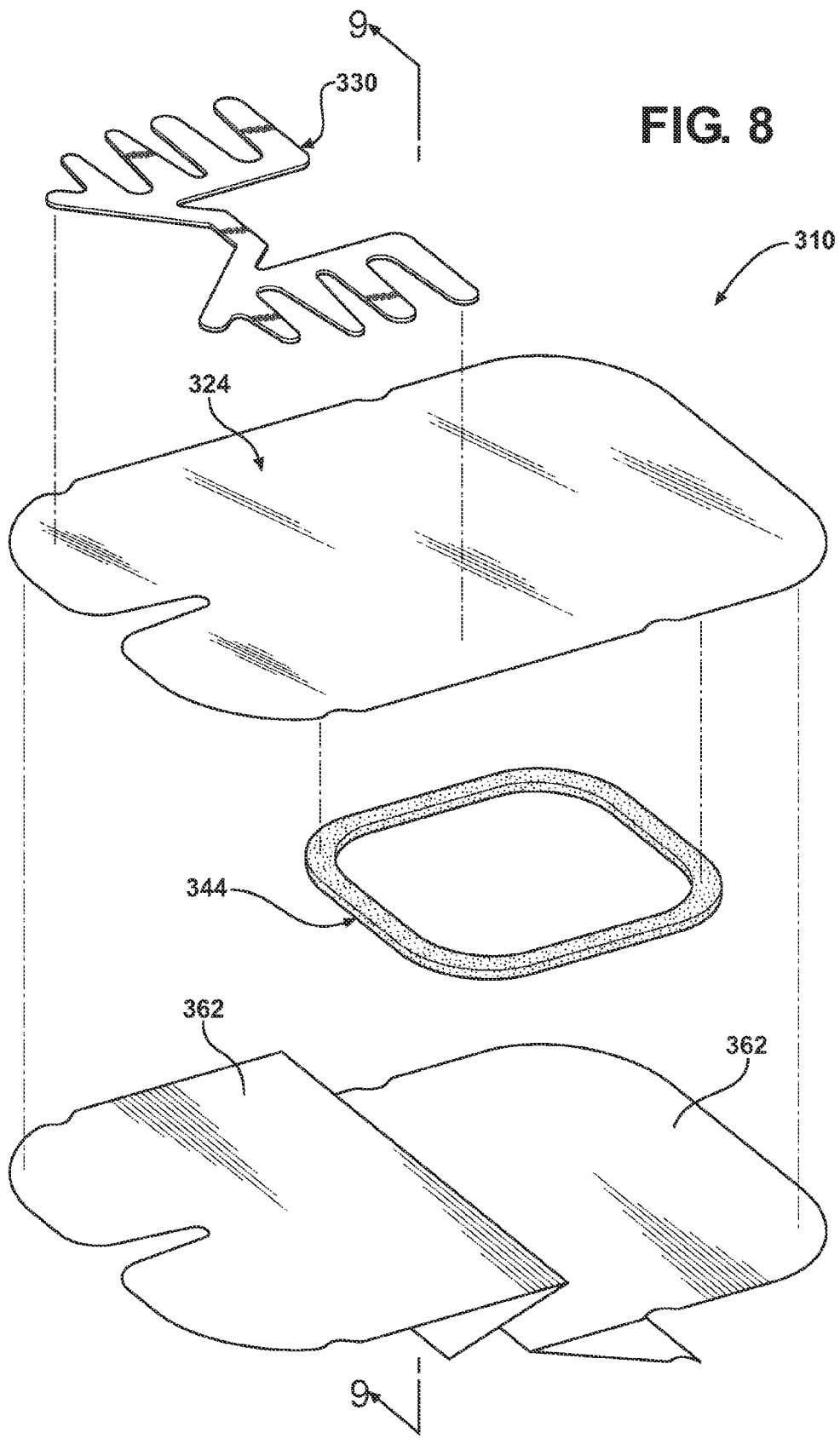
FIG. 8 is an exploded view of another alternative embodiment of a dressing with integral anchor in accordance with the present invention.
Figure 9:
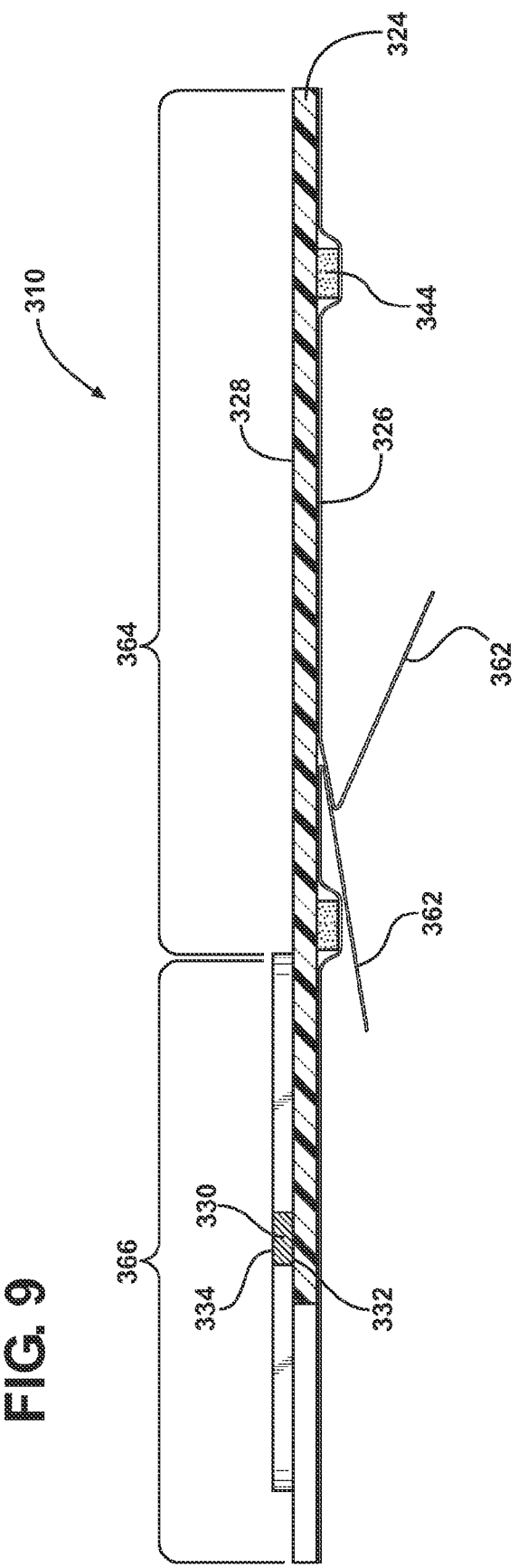
FIG. 9 is a cross-sectional view of the dressing of FIG. 8 taken along the line 9-9 in FIG. 8.

In yet another embodiment shown in FIGS. 8 and 9, a window dressing 310 in accordance with the invention includes a transparent film layer 324 having juxtaposed insertion site viewing 364 and anchor member 366 portions. The transparent film layer 324 also has an adhesive skin-adhering bottom side 326 and an opposite non-adhesive top side 328. The anchor member portion 366 includes an anchor member such as a reinforcing structure 330 disposed on the transparent film layer 324 and having an adhesive side 332 and an opposite non-adhesive side 334. The reinforcing structure adhesive side 332 is adhered to the transparent film layer non-adhesive top side 328. A pad member 344 may be adhered to the film layer adhesive side 326 in the vicinity of the insertion site viewing portion 364. A release liner 362 may cover the film layer adhesive side 326 of the insertion site viewing portion 364 and anchor member portion 366.

Figure 10:
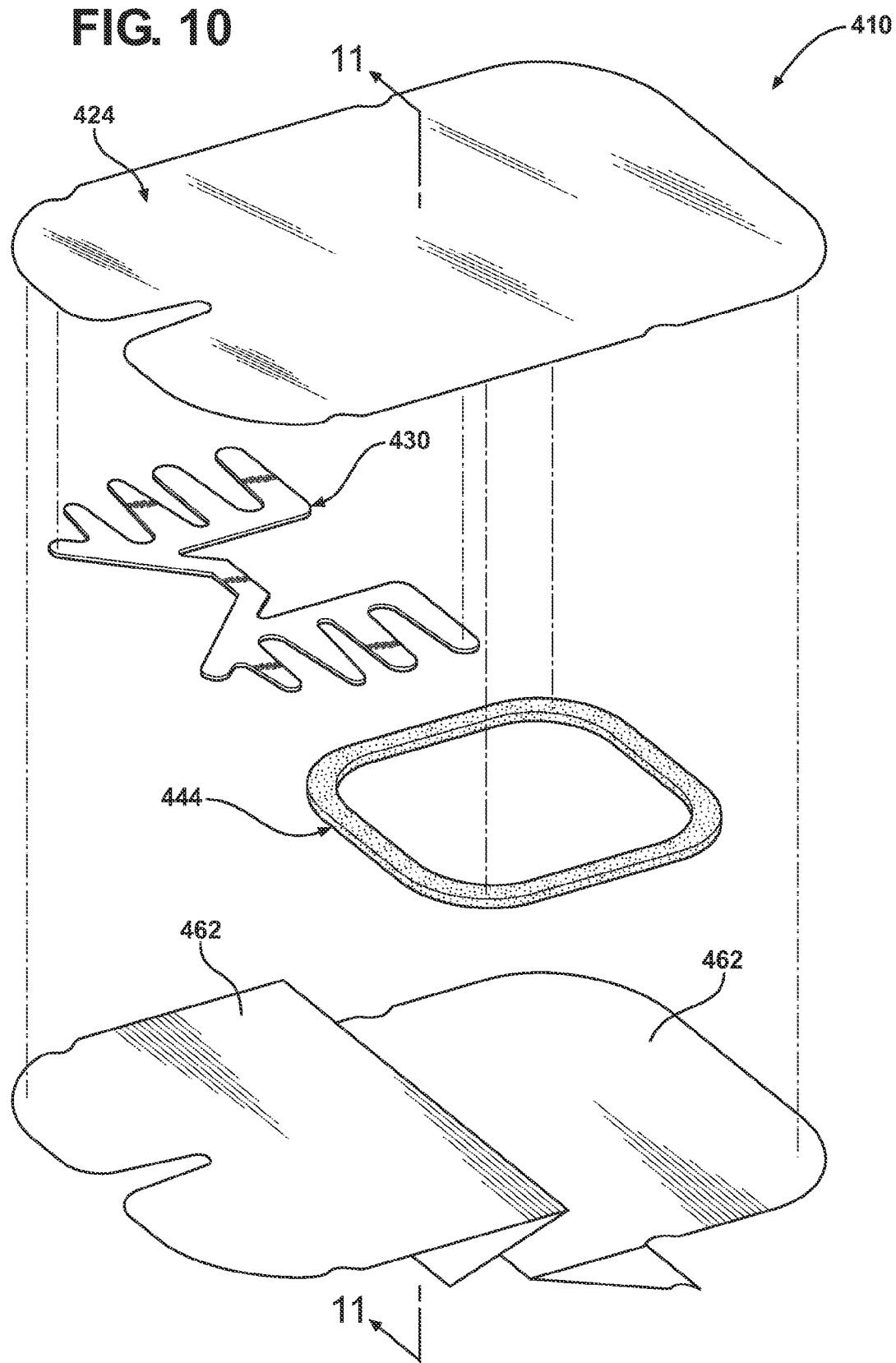
FIG. 10 is an exploded view of yet another alternative embodiment of a dressing with integral anchor in accordance with the present invention.
Figure 11:
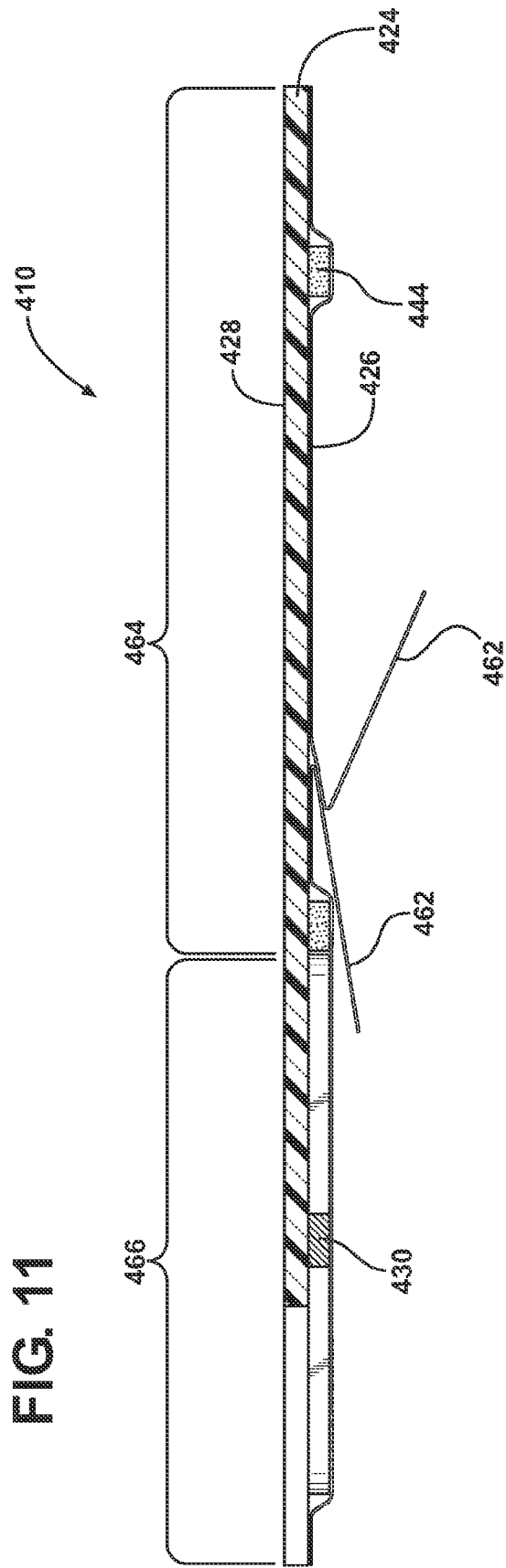
FIG. 11 is a cross-sectional view of the dressing of FIG. 10 taken along the line 11-11 in FIG. 10.

In yet another embodiment shown in FIGS. 10 and 11, a window dressing 410 in accordance with the invention includes a transparent film layer 424 having juxtaposed insertion site viewing 464 and anchor member 466 portions. The transparent film layer 424 also has an adhesive skin-adhering bottom side 426 and an opposite non-adhesive top side 428. The anchor member portion 466 includes an anchor member such as a reinforcing structure 430 disposed on the transparent film layer 424. The reinforcing structure 430 is adhered to the transparent film layer adhesive bottom side 426. A pad member 444 may be adhered to the film layer adhesive side 426 in the vicinity of the insertion site viewing portion 464. A release liner 462 may cover the film layer adhesive side 426 of the insertion site viewing portion 464 and anchor member portion 466.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A window dressing comprising:
a fabric layer having juxtaposed insertion site viewing and anchor member portions; said fabric layer having an adhesive side and an opposite non-adhesive top side;
said insertion site viewing portion being defined by an opening in said fabric layer; and
a transparent film layer having an adhesive skin-adhering, bottom side and an opposite non-adhesive side, said film layer being adhered to said fabric layer adhesive side and closing said opening in the fabric layer;
said anchor member portion including a reinforcing structure disposed on said fabric layer and having an adhesive side and an opposite non-adhesive side, said reinforcing structure adhesive side being adhered to said fabric layer non-adhesive top side.

2. The window dressing of claim 1, wherein said reinforcing structure includes a central body and a plurality of spaced ribs extending outwardly from the central body.

3. The window dressing of claim 2, wherein said reinforcing structure includes an opening in the central body.

4. The window dressing of claim 1, wherein said reinforcing structure is generally symmetric about one of its axes.

5. The window dressing of claim 1, including an opening in said anchor member portion of said fabric layer, the opening being generally surrounded by said reinforcing structure.

6. The window dressing of claim 1, including a pad member generally circumscribing said viewing portion opening and being adhered to said film layer adhesive side.

7. The window dressing of claim 1, including a U-shaped slot extending inwardly from an edge of said fabric layer.

8. The window dressing of claim 1, including a perforation line in said anchor member portion and extending from one edge of said dressing to another edge of said dressing, wherein said dressing is separable into two pieces.

9. The window dressing of claim 1, including a pair of side perforation lines, each side perforation line extending inwardly from an edge of said fabric layer proximate said opening, and being generally perpendicular to said fabric layer edge.

10. The window dressing of claim 9, including a landmark notch along the fabric layer edge at an end of each side perforation line.

11. The window dressing of claim 1, wherein said dressing is symmetrical about a longitudinal axis.

12. The window dressing of claim 1, wherein said reinforcing structure is colored.

13. The window dressing of claim 12, wherein an adhesive on said reinforcing structure adhesive side includes a colorant.

14. The window dressing of claim 12, wherein a colorant is disposed on said reinforcing structure non-adhesive side.

15. The window dressing of claim 12, wherein said reinforcing structure includes a colorant therein.

16. The window dressing of claim 1, wherein said transparent film layer extends to an outer edge of said fabric layer.

17. The window dressing of claim 1, wherein an outer edge of said fabric layer extends beyond said transparent film layer.

* * * * *